US012268685B2

(12) United States Patent
Du

(10) Patent No.: US 12,268,685 B2
(45) Date of Patent: *Apr. 8, 2025

(54) DOSING REGIMEN FOR INJECTABLE CETIRIZINE

(71) Applicant: JDP THERAPEUTICS LLC, Deerfield, IL (US)

(72) Inventor: Jie Du, Lansdale, PA (US)

(73) Assignee: JDP THERAPEUTICS LLC, Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/919,625

(22) Filed: Oct. 18, 2024

(65) Prior Publication Data

US 2025/0041289 A1 Feb. 6, 2025

Related U.S. Application Data

(63) Continuation of application No. 18/520,024, filed on Nov. 27, 2023, which is a continuation of application No. 16/656,656, filed on Oct. 18, 2019, now abandoned, which is a continuation of application No. 16/594,919, filed on Oct. 7, 2019, now Pat. No. 11,253,513.

(51) Int. Cl.
| | |
|---|---|
| *A61K 31/495* | (2006.01) |
| *A61K 9/00* | (2006.01) |
| *A61P 17/04* | (2006.01) |
| *A61P 37/08* | (2006.01) |

(52) U.S. Cl.
CPC .......... *A61K 31/495* (2013.01); *A61K 9/0019* (2013.01); *A61P 17/04* (2018.01); *A61P 37/08* (2018.01)

(58) Field of Classification Search
CPC ........ A61K 31/495; A61P 37/08; A61P 17/04; A61P 9/0019
See application file for complete search history.

(56) References Cited

U.S. PATENT DOCUMENTS

| | | | |
|---|---|---|---|
| 5,627,183 A | 5/1997 | Gray | |
| 8,263,581 B2 | 9/2012 | Du | |
| 8,314,083 B2 | 11/2012 | Du | |
| 8,513,259 B2 | 8/2013 | Du | |
| 9,119,771 B2 * | 9/2015 | Du | ........................ A61K 45/06 |
| 9,161,902 B2 | 10/2015 | Du | |
| 9,180,090 B2 | 11/2015 | Du | |
| 11,253,513 B2 * | 2/2022 | Du | ...................... A61K 31/495 |
| 2012/0010217 A1 | 1/2012 | Du | |
| 2021/0100792 A1 | 4/2021 | Du | |

OTHER PUBLICATIONS

Ampicillin for Injection, UPS For Intravenous or Intramuscular Injection; Sagent Pharmaceuticals; 2 pages; Revised Apr. 2018.
Baker, Danial E.; "Cetirizine Hydrochloride Injection"; Hospital Pharmacy; pp. 1-5; (2020); https://doi.org/10.1177/0018578720910386.
Jarvis, Paul Richard Edwin; "Improving Emergency Department Patient Flow"; Clin Exp Emerg Med 3(2); pp. 63-68; (2016).
Kelso, John M .; Patient Informatin: Anaphylaxis Symptoms and Diagnosis (Beyond the Basics); UpToDate official reprint; www.uptodate.com; pp. 1-5; Jul. 21, 2016.
Losappio et al.; Acute Urticaria Presenting in the Emergency Room of a Hospital; European Journal of International Medicine; 25; pp. 147-150; (2014).
McHugh et al.; "Improving Patient Flow and Reducing Emergency Department Crowding: A Guide for Hospitals"; AHRQ Publication No. 11(12)-0094); 48 pages; Rockville, MD: Agency for Healthcare Research and Quality; Oct. 2011.
NDA Multidisciplinary Review and Evaluation (NDA 211415) (Quzyttir (cetirizine hydrochloride injection) for intravenous use); 7 pages; Reference ID: 4501367; pp. 80-82; Version date: Oct. 12, 2018.
OFIRMEV Prescribing Information; Mallinckrodt Pharmaceuticals; PRC/FIV/0418/0031; 5 pages; revised Mar. 2018.
Richardson, Brian; Curator; "Urticaria: Cetirizine Injection Nets FDA Approval"; Clinical Essential; Drugs.com; 2 pages; Oct. 18, 2019; https://www.drugs.com/newdrugs/fda-approves-quzyttir-cetirizine-acute-urticaria-5080.html.
Salzberg et al.; "Anaphylaxis: When Seconds Count"; Emerg Med; 39(5);18, 7 pages; 2007.
Seconds Count When Dealing With Severe Food Allergies; Special to the Star; 2 pages; Dec. 21, 2017; https://www.valleymorningstar.com/2017/12/21/seconds-count-when-dealing-with-severe-food-allergies/; printed Mar. 15, 2020.
Zimmerman, Brian; "10 ICU Diagnoses With Most Opportunity to Reduce Length of Stay"; Beckers Hospital Review; Thursday, Dec. 14, 2017; printed Mar. 15, 2020; http://www.beckershospitalreview.com.
ZYRTEC Product Information Sheet 70-4573-00-6; Pfizer Labs; 13 pages; (2003).
Godse, Kiran, et al. "Busting" Urticaria with a "Burst" of Steroids, Indian J Dermatol. Nov.-Dec. 2014; 59(6): 618-619.
Peveling-Oberhag, Adriane, et al. High-Concentration Liquid Prednisolone Formula: Filling a Therapeutic Niche in Severe Acute Attacks of Urticaria and Angioedema, Skin Pharmacol Physiol 2016;29:9-12.

(Continued)

*Primary Examiner* — Timothy R Rozof
(74) *Attorney, Agent, or Firm* — Karen A. LeCuyer; DeWitt LLP

(57) ABSTRACT

Described herein is a method of administering injectable cetirizine or levocetirizine to treat acute urticaria, with or without concomitant angioedema, without life-threatening airway swelling by intravenously injecting a human patient within minutes to hours of developing acute urticaria in an emergency department or clinic with a therapeutically effective amount of an injectable cetirizine or levocetirizine composition. In the method, the injectable cetirizine or levocetirizine is the only treatment administered in the emergency department or clinic. The method can include determining, by the patient, a patient rated pruritus severity score at a 1 hour assessment, and optionally at a 2 hours assessment, and a physician discharging the human patient after 1.7±0.9 hours in the emergency department or clinic, wherein the human patient has a patient rated pruritus severity score reduction of at least 1 unit and baseline sedation at the time of discharge.

10 Claims, No Drawings

(56) References Cited

OTHER PUBLICATIONS

Pollack Jr., Charles V. & Romano, Tami, J. Outpatient Management of Acute Urticaria: The Role of Prednisone, Annals of Emergency Medicine 26:5, 1995.
U.S. Appl. No. 16/656,656, Jie Du, filed Oct. 18, 2019.
U.S. Appl. No. 16/594,919, Jie Du, filed Oct. 7, 2019.
Application No. 22-157 for Xyxal; Pharmacology Review(s); Center for Drug Evaluation and Research; Pharmacology/Toxicology Review: Amendment to Chemistry Consluit of Jul. 9, 2007, NDA No. 22-157; 135 pages; Date of review submission to Division File System (DFS): Aug. 21, 1996.
FDA; Guidance for Indusutry; "Estimating the Maximum Safe Starting Dose in Initial Clinical Trials for Therapeutics in Adult Healthy Volunteers"; 30 pages: JAGUIDANC\5541FNLCLN1. DOC; Jul. 6, 2005.
Pfizer Inc; "XYRTEC, Tablets and Syrup for Oral Use", 70-4573-00-5 Product Information; 14 pages; 2002; https://www.accessdata.fda.gov>drugsatfda_docs>label.
Pfizer Inc; "ZYRTEC-D 12 Hour," Prescribing Information; 69-5723-00-2; https://www.accessdata,fda.gov > label > 21150se8-002_zyrtec_lbl; 25 pages; printed Sep. 20, 2019.
International Search Report and Written Opinion for International Application PCT/US2020/053696; International Filing Date: Oct. 1, 2020; Date of Mailing: Dec. 1, 2020; 14 pages.
Muller, P. et al.; "The determination and interpretation of the therapeutic index in drug development"; Nature Reviews Drug Discovery, vol. 11; 2012; pp. 751-761; DOI: https://doi.org/10.1038/nrd3801.
Sampson, H. et al.; "Second symposium on the definition and management of anaphylaxis: Summary report—Second National Institute of Allergy and Infectious Disease/Food Allergy and Anaphylaxis Network symposium"; The Journal of Allergy and Clinical Immunology, vol. 117, Issue No. 2; 2006; pp. 391-397.
Zuberbier, T. et al.; "EAACI/GA2LEN/EDF/WAO guideline: definition, classification and diagnosis of urticaria"; Allergy, vol. 64; 2009; pp. 1417-1426.
Banerji et al.; Diphenhydramine Versus Nonsedating Antihistamines for Acute Allergic Reactions: A Literature Review; Allergy and Asthma Proceedings; 28(4); pp. 418-426; (2007).
PRWeb; "JDP Therapeutics Announces Positive Results From Pivotal Phase 3 Trial of QZYTIR(TM) for Acute Urticaria. Study Achieves Primary Endpoint and Key Secondary Endpoints"; PRWeb ebooks—https://www.prweb.com/releases/2018/06/prweb15585087.htm; printed Oct. 4, 2019; 4 pages; (Jun. 25, 2018).
Pulmonology Advisor; "Cetirizine Provides More Benefits for Acute Uriticaria Than Diphenhydramine"; Home_Meetings_ACAAI 2018; Nov. 16, 2018; 5 pages; Printed Oct. 4, 2019; http://www.pulmonologyadvisor.com/home/meetings/acaai-2018.

* cited by examiner

DOSING REGIMEN FOR INJECTABLE CETIRIZINE

CROSS-REFERENCE TO RELATED APPLICATIONS

This application is a continuation of U.S. application Ser. No. 18/520,024, filed Nov. 27, 2023, which is a continuation of U.S. application Ser. No. 16/656,656, filed on Oct. 18, 2019, which is a continuation of U.S. application Ser. No. 16/594,919, now U.S. Pat. No. 11,253,513 filed on Oct. 7, 2019, which are incorporated herein by reference in their entirety.

FIELD OF THE DISCLOSURE

The present disclosure is related to dosing regimens for intravenous cetirizine.

BACKGROUND

Acute allergic reaction is a systemic, immediate hypersensitivity reaction caused by exposure to a specific antigen, such as a food, insect sting, or medication. Sometimes, acute allergic reaction cannot be traced to a specific allergen. Cutaneous manifestations are most common, with acute urticaria and angioedema present in 88% or more of patients experiencing acute allergic reactions. Swelling in the airway is the most life-threatening symptom, commonly causing dyspnea, wheezing, stridor, and upper airway obstruction from severe edema. The frequency of acute allergic reaction is increasing, and this has been attributed to the increased number of potential allergens to which people are exposed, such as increased varieties of food and medications, making treatment of acute allergic reaction a critical need.

Historically, epinephrine has been the first-line drug to be given to a patient having an acute allergic reaction. Diphenhydramine injection is the second-line drug to be given to a patient having an acute allergic reaction as an adjunct therapy to epinephrine for the relief of peripheral symptoms such as pruritus, urticaria, acute urticaria, angioedema, hives, erythema, and the like. Diphenhydramine injection, however, has sedation, including severe sedation, as a common side effect, which can make it challenging to assess a patient being treated for acute allergic reaction or acute urticaria, for example. Additional side effects of diphenhydramine include cardiotoxicity (QT prolongation), an anticholinergic effect, and a potential of drug/drug interaction. In addition, diphenhydramine is short-acting, often requiring 3-4 doses per day.

Cetirizine and levocetirizine injection has been described in U.S. Pat. Nos. 9,180,090; 8,263,581; 9,119,771; 8,513,259; 8,314,083; and 9,161,902 for the treatment of acute urticaria and acute angioedema associated with an acute allergic reaction such as anaphylaxis. Unexpectedly, the cetirizine injection is free of hemolysis, which is a significant problem for cetirizine's parent molecule, hydroxyzine. Also unexpectedly, cetirizine injection has a peak plasma concentration (Cmax) greater than twice the Cmax of a comparable immediate-release oral cetirizine dosage form, while having a similar area under the plasma time curve. Advantageously, cetirizine injection provides a less sedating alternative to, for example diphenhydramine injection.

While the safety of oral cetirizine has been studied extensively and oral cetirizine is known to be safe at very high oral doses, the safety of intravenous cetirizine has not been studied in detail. What is needed are dosing regimens for safe and effective dosing of intravenous cetirizine.

BRIEF SUMMARY

In one aspect, a method of administering injectable cetirizine or levocetirizine comprises intravenously injecting a mammal in need thereof with a therapeutically effective amount of an injectable cetirizine or levocetirizine composition, wherein the mammal receives a maximum daily dose of the cetirizine or levocetirizine that is no more than 15 times a maximum recommended daily clinical dose for the mammal.

In another aspect, a method of administering injectable cetirizine or levocetirizine comprises intravenously injecting a mammal in need thereof with a therapeutically effective amount of an injectable cetirizine or levocetirizine composition at least once per day, wherein the daily cetirizine or levocetirizine is repeated for no more than 5 consecutive days.

In yet another aspect, a method of administering injectable cetirizine dihydrochloride comprises intravenously injecting a mammalian subject in need thereof with an effective amount of an injectable cetirizine dihydrochloride composition, wherein a maximum daily dose of the cetirizine dihydrochloride is a human equivalent dose of 13 mg/kg in rats, or 2.1 mg/kg, or 15 times the maximum recommended human clinical dose.

In a further aspect, a method of administering injectable cetirizine dihydrochloride comprises intravenously injecting a mammalian subject in need thereof with a therapeutically effective amount of an injectable cetirizine dihydrochloride composition, wherein a maximum daily dose of the cetirizine dihydrochloride is greater than the maximum recommended daily dose and less than the human equivalent of 35 mg/kg in rats.

In another aspect, a method of administering injectable cetirizine or levocetirizine comprises intravenously injecting a human patient in an emergency department or clinic with a therapeutically effective amount of an injectable cetirizine or levocetirizine composition, wherein the human patient spends 1.7±0.9 hours in the emergency department or clinic.

The above-described and other features will be appreciated and understood by those skilled in the art from the following detailed description and appended claims.

DETAILED DESCRIPTION

Unexpectedly, as described herein, while oral cetirizine has an extremely good safety margin in rats, cetirizine injection was found to have a safety margin that is much lower than the oral dose. This result was particularly surprising as the area under the curve (AUC) for oral and intravenous injection of 10 mg of cetirizine was found to be equivalent, leading to the expectation that intravenous cetirizine would have a similar safety margin to oral cetirizine. In addition, as described in the toxicology report for New Drug Application No. 022157 for Xyzal® levocetirizine solution, intravenous levocetirizine and cetirizine were previously shown to have a similar safety margin as oral cetirizine and levocetirizine when tested in mice.

In addition, while oral cetirizine can be used for daily, that is chronic administration for weeks, months and even years, the data provided herein suggests that cetirizine injection should not be continued for more than 5 consecutive days, particularly at a dose above the maximum recommended clinical dose such as 17 times the maximum recommended clinical dose. These important conclusions provide safe and effective dosing of intravenous cetirizine.

In the studies described herein, injectable cetirizine dihydrochloride was intravenously administered once daily to Sprague Dawley rats for 14 consecutive days. The highest no observable adverse effect level (NOAEL) in rats was established at 13 mg/kg/day (15 times the human clinical dose). Toxicity was observed at injectable cetirizine dihydrochloride doses higher than 15 mg/kg/day in rats (17 times of human clinical dose) on once daily intravenous administration repeated for 5 consecutive days. The maximum tolerated dose (MTD) of injectable cetirizine dihydrochloride was established at 35 mg/kg for a single intravenous injection. Injectable cetirizine dihydrochloride administration to the Sprague Dawley rat was associated with mortality at dose levels ≥50 mg/kg for a single IV injection.

Specifically, rat studies were performed because it is a rodent species recommended by various regulatory authorities for studies of this type. As evidenced by the US FDA Guidance for Industry: Estimating the Maximum Safe Starting Dose in Initial Clinical Trials for Therapeutics in Adult Healthy Volunteers, 2005, determining the no observed adverse effect levels (NOAELs) in an animal model such as mouse or rat is a benchmark for safety which can be converted to a human equivalent dose (HED) according to a standard conversion based on body surface area. Based on the 13 mg/kg NOAEL in rats, the HED can be calculated as follows:

Human clinical dose=10 mg in a 70 kg human=0.14 mg/kg human.

Using the x6 conversion factor between rats and human, equivalent rat dose=0.14×6=0.86 mg/kg rat (i.e., 0.86 mg/kg in rat=10 mg in human (human clinical dose))

Therefore 13 mg/kg in rat=15 times of human clinical dose (=13 divided by 0.86) 13 mg/kg in rats corresponds to 2.16 mg/kg in humans.

Cetirizine, (±)-[2-[4-[(4-chlorophenyl) phenylmethyl]-1-piperazinyl] ethoxy] acetic acid, dihydrochloride, is a selective H1-receptor antagonist. Cetirizine is a racemic mixture, and levocetirizine refers to the R-isomer of cetirizine. According to the ZYRTEC® Prescribing Information, the acute minimum lethal oral dose in mice is 237 mg/kg (approximately 95 times the maximum recommended daily dose in adults), and in rats the acute minimum lethal oral dose is 562 mg/kg (approximately 460 times the maximum recommended daily dose in adults).

As used herein, a maximum recommended daily dose is the maximum recommended dose to be administered over a 24 hour period. As used herein, daily refers to a 24 hour period.

In an aspect, a method of administering injectable cetirizine or levocetirizine comprises intravenously injecting a mammalian subject in need thereof with a therapeutically effective amount of an injectable cetirizine or levocetirizine composition, wherein the mammal receives a maximum daily dose of the cetirizine or levocetirizine that is no more than 15 times a maximum recommended daily clinical dose for the mammal. In an aspect, the maximum daily dose of the cetirizine or levocetirizine provides a highest no observable adverse effect level of the cetirizine or levocetirizine.

In another aspect, method of administering injectable cetirizine or levocetirizine comprises intravenously injecting a mammal in need thereof with a therapeutically effective amount of an injectable cetirizine or levocetirizine composition at least once per day, wherein the daily cetirizine or levocetirizine is repeated for no more than 5 consecutive days, particularly when in an overdose situation such as at doses of 17 times the recommended clinical dose. In an aspect, repeating daily cetirizine dihydrochloride injection for no more than 5 consecutive days reduces toxicity.

In yet another aspect, a method of administering injectable cetirizine dihydrochloride comprises intravenously injecting a mammalian subject in need thereof with an effective amount of an injectable cetirizine dihydrochloride composition, wherein a maximum daily dose of the cetirizine dihydrochloride is a human equivalent dose of 13 mg/kg in rats, or 2.1 mg/kg, or 15 times the maximum recommended human clinical dose. In an aspect, the maximum daily dose of the cetirizine dihydrochloride is about 150 mg for a 70 kg weight human. In another aspect, the maximum daily dose of the cetirizine dihydrochloride is a human equivalent dose of 35 mg/kg in rats, which is the highest tolerated dose. In another aspect, the maximum daily dose of the cetirizine dihydrochloride is a human equivalent dose of 15 mg/kg in rats, which is the highest tolerated dose when administered for 5 consecutive days. In another aspect, the maximum daily dose of the cetirizine dihydrochloride is a human equivalent dose of 13 mg/kg in rats, which is the highest tolerated dose when administered for 14 consecutive days.

In yet another aspect, a method of administering injectable cetirizine dihydrochloride comprises intravenously injecting a mammalian subject in need thereof with a therapeutically effective amount of an injectable cetirizine dihydrochloride composition, wherein a maximum daily dose of the cetirizine dihydrochloride is greater than the maximum recommended daily dose and less than the human equivalent of 35 mg/kg in rats.

In an aspect, the therapeutically effective amount of the injectable cetirizine or levocetirizine composition is greater than the maximum recommended daily clinical dose for the mammal. In a further aspect, the therapeutically effective amount of the injectable cetirizine or levocetirizine composition is an overdose of 2, 3, 4, 5, 6, 7, 8, 9, 10, 11, 12, 13, or 14 times the maximum recommended daily clinical dose for the mammal.

As used herein, an overdose is a dose greater than the maximum recommended daily clinical dose. An overdose can be intentional or accidental. For example, a parent or health care worker may provide a child with an adult dose. A physician or health care worker may prescribe, administer or suggest an overdose if a patient's symptoms are very serious, or if the patient is not responding to the maximum recommended daily clinical dose. A patient may request to be administered an overdose if not responding to the maximum recommended daily clinical dose.

Cases of adult and pediatric patients with overdoses of only oral cetirizine hydrochloride have been reported, some of which resulted in adverse reactions. Adult overdose cases involved patients 18 to 81 years of age receiving oral cetirizine hydrochloride doses of 70 mg to 800 mg (7 to 80 times the maximum recommended dosage of 10 mg/day in adults). The most commonly reported adverse reactions were somnolence and fatigue. Other reported adverse reactions included tachycardia, abdominal pain, nausea, and vomiting. Pediatric overdose cases involved patients 18 months to 15 years of age receiving oral cetirizine hydrochloride doses of 90 mg to 300 mg (9 to 72 times the maximum age recommended dose). The adverse reactions reported included: somnolence, difficulty walking, agitation/irritability, hard to swallow/articulate clearly, tachycardia, vomiting, mydriasis, and elevated creatinine phosphokinase.

Overdosing instructions are important for drug safety because, as shown herein, the safety margin for injectable cetirizine and levocetirizine is much smaller than for the oral forms. The instructions disclosed herein will change clinician's expectation and approach for dosing cetirizine which is based on dosing oral cetirizine for the past 30 years.

While the data provided herein was for cetirizine dihydrochloride, one of ordinary skill in the art would understand that the results would be expected to be similar for cetirizine free base, other salts of cetirizine, levocetirizine free base, and salts of levocetirizine such as levocetirizine hydrochloride. For example, 10 mg of cetirizine hydrochloride is the equivalent of 8.42 mg cetirizine free base.

Exemplary mammalian subjects include humans, including adults and children, mice, hamsters, rats, ferrets, guinea pigs, rabbit, dogs, primates, pigs and mini-pigs. In an aspect, the mammal is a human. Animal doses in mg/kg can be converted to human equivalent doses in mg/kg according to the following table:

| Species | To convert animal dose in mg/kg to human dose in mg/kg, divide the animal dose by =: |
|---|---|
| mouse | 12.3 |
| hamster | 7.4 |
| rate | 6.2 |
| ferret | 5.3 |
| guinea pig | 4.6 |
| rabbit | 3.1 |
| dogs | 1.8 |
| monkey | 3.1 |
| pig | 1.4 |
| mini-pig | 1.1 |

When the mammal is a human subject, the recommended human daily clinical dose is 2.5, 5 or 10 mg of cetirizine dihydrochloride administered once daily. One of ordinary skill in the art would understand that an equivalent dose of cetirizine base could also be employed.

In specific aspects, wherein the human subject is a child 6 months to 5 years and the maximum recommended human daily clinical dose of cetirizine dihydrochloride is 2.5 mg; the human subject is a child 6 to 11 years and the recommended human daily clinical dose of cetirizine dihydrochloride is 5 or 10 mg; or the human subject is an adult of adolescent 12 years or older and the maximum recommended daily clinical dose of cetirizine dihydrochloride is 10 mg.

When the mammal is a human subject, the recommended human daily clinical dose is 1.25, 2.5 or 5 mg of levocetirizine dihydrochloride administered once daily. One of ordinary skill in the art would understand that an equivalent dose of levocetirizine base could also be employed.

In specific aspects, wherein the human subject is a child 6 months 5 years and the recommended human daily clinical dose of levocetirizine dihydrochloride is 1.25 mg; the human subject is a child 6 to 11 years and the recommended human daily clinical dose of levocetirizine dihydrochloride is 2.5 or 5 mg; or the human subject is an adult of adolescent 12 years or older and the recommended daily clinical dose of levocetirizine dihydrochloride is 5 mg.

In an aspect the mammalian subject is suffering from acute urticaria, with or without concomitant angioedema Symptoms of acute allergic reactions include pruritus, erythema, angioedema, acute urticaria, urticaria areas, erythema areas, wheezing, and the like. Exemplary patients susceptible to acute allergic reactions include patients with food allergies (peanuts, other nuts, seafood, and the like), patients with exercise induced allergies, patients allergic to insect stings, patients with poison ivy induced allergies, and the like. Additional patients include those already in the hospital experiencing drug induced allergies to: antibiotics, IV contrast media, anesthesia, aspirin/NSAIDs, opioids, chemotherapy agents, muscle relaxants, latex gloves, blood materials, and the like. Acute allergic reactions can present symptoms within minutes to hours of exposure to a triggering substance. Severe acute allergic reactions often require treatment in emergency rooms or urgent care centers.

As used herein, acute urticaria means a short-term skin condition characterized by hives, which are red, itchy welts resulting from a skin reaction. Urticaria is often attended by severe pruritus. Acute urticaria is one of the most visible signs of acute allergic reactions such as anaphylaxis. Acute Urticaria may be accompanied by angioedema, or swelling of the skin.

In another aspect, in clinical trials, the proportion of patients returning to any emergency department or clinic was lower in the injectable cetirizine treatment group (6%) compared to the diphenhydramine treatment group (14%), and the time spent in the treatment center (hours spent reported as mean (SD) was shorter in the injectable cetirizine treatment group (1.7 (0.9)) compared to the diphenhydramine treatment group (2.1 (1.1)).

In an aspect, a method of administering injectable cetirizine or levocetirizine comprises intravenously injecting a human patient in an emergency department or clinic with a therapeutically effective amount of an injectable cetirizine or levocetirizine composition, wherein the human patient spends 1.7±0.9 hours in the emergency department or clinic. In an aspect, the therapeutically effective amount is the maximum recommended daily clinical dose. In an aspect, the human patient does not return to the emergency department or clinic. In another aspect, the human patient returns to the emergency department or clinic. In another aspect, the human patient has acute urticaria.

The injectable cetirizine or levocetirizine can be in unit dose form in ampoules, small volume parenteral (SVP) vials, large volume parenterals (SVP), pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, buffering, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

Parenteral injectable formulations are typically aqueous solutions which may contain excipients such as salts, carbohydrates and buffering agents (preferably at a pH of from 3 to 9.5), but, for some applications, they may be more suitably formulated as a sterile non-aqueous solution or as a dried form to be used in conjunction with a suitable vehicle such as sterile, pyrogen-free water.

An exemplary cetirizine dihydrochloride composition is a 10 mg/ml aqueous solution, optionally isotonic. In an aspect, the cetirizine dihydrocloride composition is QUZYTTIR™.

The invention is further illustrated by the following non-limiting examples.

EXAMPLES

Example 1

Escalating Dose and 7-Day Repeat Dose Intravenous Administration Toxicity Study in Sprague-Dawley Rats

Background

The study was conducted in four phases (Phase I, II/IIB, III and IV/IVB) via various methods of intravenous injection to rats. The intravenous route is the route of administration for the final finished product in human subjects. The objective of the Dose Escalating Phase (Phase I) of the study was to determine the maximum tolerated dose (MTD) of the test item, cetirizine dihydrochloride, following a single intravenous bolus injection to the rat. The Repeat Dose Phase (Phase II/IIB and III) was then performed to determine the toxicity of the test item, when administered once daily by intravenous injection to rats for 7 consecutive days. Phase III was conducted to evaluate repeat dosing using a Sponsor prepared human clinical formulation.

Phase IV/IVB was conducted to test the viability of administering the test item (i.e., cetirizine dihydrochloride injection at 10 mg/mL) intravenously into the femoral vein over a period of 5 days, and mainly to observe if the lower dose eliminated the hematuria (red colored urine). Table 1 summarizes the four phases.

TABLE 1

Summary of 4 study phases

| Phase | Rationale and Objective | Dose Level (mg/kg) | Conc (mg/mL) | Vol (mL/kg) | Injection Duration (minutes) | Injection Location | Conclusion |
|---|---|---|---|---|---|---|---|
| Phase I | Dose escalation to determine the MTD | 1 to 100 | 0.2 to 20 | 5 | 2 minutes | Tail vein | MTD established at 35 mg/kg |
| Phase II | Repeated dose for 7 days at 35 mg/kg | 35 | 7 | 5 | 2 | Tail vein | Injection site swelling and necrosis, incomplete repeat phase. |
| Phase IIB | Repeated dose for 7 days at 30 mg/kg. Dose formulation adjusted for pH. | 30 | 3 | 10 | 20 | Tail vein | Injection site swelling, absence of necrosis. Repeat phase completed for majority of animals. |
| Phase III | Repeated dose for 7 days at 30 mg/kg using Sponsored prepared formulation | 30 | 10 | 3 | 2 | Tail vein | Tail vein swelling and necrosis, incomplete repeat phase. |
| Phase IV | Phase IIB had injection site irritation on the tail vein. This phase was to test the viability of administering the test item intravenously to the femoral vein for 5 days. | 30 | 10 | 3 | 2 | Femoral vein | Hematuria (red colored urine), changes in posture increase in activity |
| Phase IVB | To test lower doses to observe if there was hematuria | 7 and 15 | 10 | 0.7 and 1.5 | 2 | Femoral Vein | Hematuria (red colored urine), urine seen at 15 mg/kg. Changes in posture and hyperactivity seen at 7 mg/kg. |

Methods

Phase I (Dose escalation): The test item dose formulation was administered in an escalating dose fashion by slow intravenous injection (over approximately 2 minutes) into the tail vein using a hypodermic needle attached to a syringe. A minimum 24-hour observation period was allowed between successive doses. The dose volume was 5 mL/kg for all animals. The actual volume administered to each rat was calculated and adjusted based on the most recent practical body weight of each animal. The protocol is described in Table 2.

TABLE 2

Phase I (Dose escalation) protocol

| Group Numbers | Treatment on Study Day | Dose Level (mg/kg) | Dose Conc. (mg/mL) | Dose Volume (mL/kg)* | Number of Main Animals Males | Number of Main Animals Females | Number of TK Animals Males | Number of TK Animals Females |
|---|---|---|---|---|---|---|---|---|
| 1 | 1 | 1 | 0.2 | 5 | 2 | 2 | — | — |
| 2 | 2 | 100 | 20 | 5 | 2 | 2 | — | — |

TABLE 2-continued

Phase I (Dose escalation) protocol

| Group Numbers | Treatment on Study Day | Dose Level (mg/kg) | Dose Conc. (mg/mL) | Dose Volume (mL/kg)* | Number of Main Animals Males | Number of Main Animals Females | Number of TK Animals Males | Number of TK Animals Females |
|---|---|---|---|---|---|---|---|---|
| 3 | 3 | 25 | 5 | 5 | 2 | 2 | — | — |
| 4 | 4 | 50 | 10 | 5 | 2 | 2 | — | — |
| 5 | 5 | 35 | 7 | 5 | 2 | 2 | — | — |
| 6 | 8 | 35 | 7 | 5 | — | — | 2 | 2 |

TK = Toxicokinetic
*Dosing was via a 2 min intravenous slow push

All surviving Main animals were observed for 14 days after dosing, following which they were euthanized and their carcasses were discarded without further examination.

TK animals were euthanized and discarded without further examination following collection of their last blood sample on Day 1.

Phase II (Repeat Dose): The test item dose formulation was administered once daily by slow bolus intravenous injection (over approximately 2 minutes) for 3 consecutive days into the tail vein using a hypodermic needle attached to a syringe. The dose volume was 5 mL/kg for all animals. The actual volume administered to each rat was calculated and adjusted based on the most recent practical body weight of each animal. The protocol is described in Table 3.

TABLE 3

Phase II (Repeat Dose) protocol

| Group Number | Dose Level (mg/kg) | Dose Concentration (mg/mL) | Dose Volume (mL/kg)* | Number of Animals Males | Number of Animals Females |
|---|---|---|---|---|---|
| 7 | 35 | 7 | 5 | 5 | 5 |

*Dosing was via a 2 min intravenous slow push

After 3 days of consecutive dosing the injection sites were not viable. All surviving animals were euthanized and discarded without further examination.

Phase III (Repeat Dose): The test item dose formulation was administered once daily by slow bolus intravenous injection (over approximately 2 minutes) for 2 consecutive days into the tail vein using a hypodermic needle attached to a syringe. The dose volume was 3 mL/kg for all animals. The actual volume administered to each rat was calculated and adjusted based on the most recent practical body weight of each animal. The protocol is described in Table 4.

TABLE 4

Phase III (Repeat Dose) protocol

| Group Number | Dose Level (mg/kg) | Dose Concentration (mg/mL) | Dose Volume (mL/kg)* | Number of Animals Males | Number of Animals Females |
|---|---|---|---|---|---|
| 8 | 30 | 10 | 3 | 5 | 5 |

*Dosing was via a 2 min intravenous slow push

After 2 days of dosing the injection sites were not viable. The animals were euthanized on Day 3 and subjected to a necropsy examination.

Phase IIB (Repeat Dose): The test item dose formulation was administered once daily by intravenous infusion (over approximately 20 minutes) for 7 consecutive days into the tail vein using an abbocath. The dose infusion rate was 30 mL/kg/hour (10 mL/kg or 0.5 mL/kg/minute) for all animals. The actual volume infused per hour was calculated and adjusted based on the most recent body weight of each animal. The infusion rate was controlled using an infusion pump. Prior to onset of each treatment, the infusion line was pre-filled with the appropriate dose formulation to ensure that dosing started as soon as the infusion pump was turned on. The protocol is described in Table 5.

TABLE 5

Phase IIB (Repeat Dose) protocol

| Group Number | Dose Level (mg/kg) | Dose Concentration (mg/mL) | Number of Animals Males | Number of Animals Females |
|---|---|---|---|---|
| 9 | 30 | 3 | 5 | 5 |

The infusion rate was 30 mL/kg/hour (0.5 mL/kg/minute) which over a 20 minute duration was a dose volume of 10 mL/kg.

Upon completion of the 7-day dosing period, all surviving animals were euthanized (Day 8) and subjected to a necropsy examination.

Phase IV: The test item was administered intravenously at a dose volume of 3 mL/kg for 5 consecutive days over a period of 2 minutes. The actual volume administered was calculated and adjusted based on the most recent body weight of each animal. Prior to onset of each treatment, a bolus was given to fill the line. The remaining volume to be administered (taking into account the pre-filled bolus) was administered. The line was flushed with saline. The injection duration was 2 minutes from the time that the initial volume of test item had been administered to the end of the saline flush. Following the flush the animals were attached to the infusion system for saline maintenance. The protocol is described in Table 6.

TABLE 6

Phase IV protocol

| Group Number | Dose Level (mg/kg) | Dose Concentration (mg/mL) | Number of Animals Males | Number of Animals Females |
|---|---|---|---|---|
| 10 | 30 | 10 (Sponsor's clinical final product) | 2 | 2 |

The dose volume was 3 mL/kg.

Upon completion of the 5-day dosing period, all surviving animals were euthanized (Day 6) and subjected to a necropsy examination.

Phase IVB: The test item was administered intravenously at a dose volume of 0.7 or 1.5 mL/kg for 5 consecutive days over a period of 2 minutes. The actual volume administered was calculated and adjusted based on the most recent body weight of each animal. Prior to onset of each treatment, a bolus was given to fill the line. The remaining volume to be administered (taking into account the pre-filled bolus) was administered. The line was flushed with saline. The injection duration was 2 minutes from the time that the initial volume of test item had been administered to the end of the saline flush. Following the flush the animals were attached to the infusion system for saline maintenance. The protocol is described in Table 7.

TABLE 7

Phase IVB protocol

| Group Number | Dose Level (mg/kg) | Dose Concentration (mg/mL) | Number of Animals | |
|---|---|---|---|---|
| | | | Males | Females |
| 11 | 7 | 10 (Sponsor's clinical final product) | 1 | 1 |
| 12 | 15 | 10 (Sponsor's clinical final product) | 1 | 1 |

The dose volume was 0.7 mL/kg for Group 11 and 1.5 mL/kg for Group 12.

Upon completion of the 5-day dosing period, all surviving animals were euthanized and discarded without further examination. Particular attention was paid to clinical signs observed following dosing. Specifically, the occurrence of any hematuria was documented.

Animals for each group were assigned to different replicates for logistical reasons. Animals in replicates A to F were used in Phase I and Replicates G, H and I animals were assigned to Phase II. Replicate J animals were used for Phase III. Replicate K animals were used in Phase IIB. Replicate L animals were used in Phase IV. Replicate M animals were used in Phase IVB.

The initial dose level (Phase I) was based on data collected for the human intravenous clinical dose of 0.143 mg/kg (10 mg per dose). This intravenous dose was previously studied in human clinical phase I, II and III trials. There are abundant toxicology data on cetirizine via the oral route, and but no data available on the IV injection route. However, from a human pharmacokinetics study, 10 mg cetirizine IV injection had an equivalent AUC as the 10 mg oral product, and ~3.8 times of the $C_{max}$ of the 10 mg oral product. There is a significant amount of literature and the tolerance of the test item has been well established at the human clinical dose. Subsequent dose levels in Phase I were determined based on the animals reaction to the previous dose. Dose levels for Phase II and III were selected based on the results obtained in Phase I and/or II. For Phase IIB, the drug administration procedure was a 30 mg/kg dose-via-tail vein.

The dose level selected for Phase IV was based on the results obtained in Phase IIB and Phase III. In Phase IIB and III, local irritation at the dosing site (tail vein) was a factor in limiting the placement of the abbocath at the dosing site. In order to avoid local irritation effects, intravenous injection of the test item into a surgically catheterized femoral vein was tested in Phase IV. Due to the differences in circulatory mechanics between the tail vein (very limited blood circulation) and the femoral vein (significantly more blood circulation than tail vein), the femoral vein was considered to be a better approximation of the human intravenous injection site. The injected drug solution was expected to be quickly diluted by blood circulation and therefore minimizing the local irritation potential. Therefore, it was believed local irritation was less likely to occur when the test item was given through the femoral vein.

In all cases, the test item was 10 mg/ml cetirizine hydrochloride dissolved in sodium chloride for injection, USP.

Test Animals

Sprague-Dawley rats were used for all of the experiments.

Housing: Rats were housed in groups of up to 3 of the same sex (except during designated procedures) in bins made of transparent plastic with dimensions of 25.4 cm×48.3 cm×20.3 cm equipped with an automatic watering system supplemented by water bottles as appropriate. The bottom of the plastic bins were covered by an at least 2 cm layer of bedding (Beta chip®). Bedding was changed at appropriate intervals to maintain hygienic conditions. Following randomization, all cages were labeled with a color-coded cage card indicating study number, group, animal number, sex and group designation.

Room environment: The animal room environment was controlled (targeted ranges: temperature 21±3° C., relative humidity 50±20%, 12 hours light, 12 hours dark, a minimum of 10 air changes per hour) except during designated procedures such as during out of hours blood collections. Temperature and relative humidity was monitored continuously and records maintained at ITR.

Diet/water: A standard certified commercial rodent chow (Envigo Global 18% Protein Rodent Dict #2018C) was provided to the animals ad libitum except during designated procedures such as those requiring removal of the animal from the home cage. Concentrations of the constituents of the diet and environmental contaminants are routinely measured by the manufacturers (Batch certificates on file at ITR).

Municipal tap water (which was purified by reverse osmosis, ultraviolet light and further filtered with a 0.2 µm filter) was provided to the animals ad libitum except during designated procedures. Periodic analyses of municipal tap water (collected by the municipality) and reverse osmosis water from the animal rooms (collected by ITR) are performed by Eurofins Canada, Pointe-Claire, Quebec, Canada and the results are retained on file at ITR.

Environmental Enrichment: During the study the animals were offered non-dictary items (nylabones®, diamond nests, diamond twists) and were offered certified treats (supreme minitreats™, yogurt drops) as part of the ITR environmental enrichment program, at appropriate intervals, except during designated procedures.

Acclimation: A minimum 2-week acclimation period was allowed between receipt of the animals and the start of treatment to accustom the rats to the laboratory environment. Acclimatization to restraint or dosing procedures were performed as per ITR SOPs.

Allocation to study groups: During the acclimation period for Phases I/II, 17 male and 17 female rats were assigned to their respective dose groups (1 to 7) by block randomization based on body weights. Males and females were randomized separately. For Phase III, during the acclimation period, 5 male and 5 female rats were randomly assigned to the dosing Group 8. For Phase IIB, during the acclimation period, 5 male and 5 female rats were randomly assigned to the dosing Group 9. For Phase IV, during the acclimation period, 2 male and 2 female rats were randomly assigned to the dosing Group 10. For Phase IVB, during the acclimation period, 2 male and 2 female rats from the ITR Spare Colony were randomly assigned to the dosing Groups 11 and 12. Certain animals were replaced due to difficulty dosing or clinical signs noted at the injection site.

Toxicokinetics: Sample Collection, Processing and Bioanalysis: A series of 5 blood samples (approximately 0.4 mL each) was collected from each Group 6 rat at pre-dose, 2, 6, 15 and 30 minutes after treatment. Thus, a total blood volume of 2.0 mL was taken from each rat during the course of the study. For this purpose, each rat (unanesthetized) was bled by jugular venipuncture and the samples were collected into tubes containing the anticoagulant, $K_2EDTA$. Tubes were placed on wet ice pending processing. Following its last blood sampling, each animal was euthanized by $CO_2$ asphyxiation followed by cervical dislocation and discarded without further examination. In-life observations (clinical signs [when present] and body weights) for these animals were recorded but not reported. Following collection, the samples were centrifuged (2500 rpm for 10 minutes at approximately 4° C.) and the resulting plasma was recovered and stored frozen (≤−60° C.) in appropriately labeled tubes.

Necropsy Procedures: Gross Examination: All surviving Phase I animals were observed for 14 days after dosing, following which they were euthanized (Day 15) and their carcasses were discarded without further examination. Phase IVB animals were euthanized and discarded without further examination following completion of the treatment period (Day 6). All Phase IIB and III/IV animals were euthanized and subjected to a necropsy examination upon completion of the treatment period and following an overnight period without food on Day 8. These animals were anesthetized with isoflurane, then euthanized by exsanguination. In order to avoid autolytic changes, the necropsy examination of the carcass was conducted, as soon as possible, on all animals of Phases IIB/III/IV which were euthanized at the study conclusion. Gross pathology consisted of an external examination, including identification of all clinically-recorded lesions, as well as a detailed internal examination. A staff pathologist was available for consultation during all necropsies performed during regular working hours.

Tissue Preservation: On completion of the gross pathology examination and selected organ weighing, the tissues and organs noted below were retained. Neutral buffered 10% formalin was used for fixation and preservation unless otherwise indicated.

Data Evaluation and Statistics: Numerical data obtained during the conduct of the study were subjected to calculation of group means and standard deviations and were presented in the final report along with all individual numerical and non-numerical results.

Results

Mortality: In Phase I, mortality was noted immediately post-dosing at 50 (Group 2) and 100 mg/kg (Group 4). $2/4$ Group 2 and $3/4$ Group 4 animals were found dead. The surviving Group 2 animals were not dosed due to the mortality noted. Clinical sign onset was rapid and included labored/decreased respiration, tremors, loss of coordination and limb function and severely decreased activity.

All Phase III animals (Group 8, at 30 mg/kg/day) were pre-terminally euthanized on Day 3. These animals were euthanized due to the test item related clinical signs as of Day 2 noted at the injection site (tail) which made dosing impossible. The clinical signs noted at the injection site included: swelling, bruising, presence of liquid and discoloration. The discoloration noted was primarily bluish to black in color indicative of pre-necrotic and necrotic tissue formation. Perivenous leakage was not a cause of the changes. These clinical signs were noted as of Day 2. Increases in activity and respiration were noted during dosing on Day 1.

Clinical Signs: In Phase I, single administration of the test item at 1 (Group 1), 25 (Group 3) and 35 (Groups 5 and 6) mg/kg was well tolerated and no adverse clinical signs were noted.

In Phase II, tail vein injection over 2 minutes, $3/5$ male and $2/5$ female (Group 7, at 35 mg/kg/day) were pre-terminally euthanized due to test item related changes noted at the dosing site. In order to verify the initial findings noted in Group 7 animals, the euthanized animals were replaced and the replacements dosed. However, the initial observations of injection site irritation noted in the original animals were confirmed in the replacement animals. The clinical signs for these animals included: activity increase, swelling at the injection site, discoloration at the dosing site, lesions and red spotting at the dosing site, dosing site sensitive to touch, licking of the injection site and vocalization prior to dosing (indicative of a pain response). The clinical signs noted at the injection site were noted as early as Day 2. Increases in activity were noted during dosing as of Day 1.

For Phase IIB, tail vein infusion for 20 minutes, animals (Group 9, at 30 mg/kg/day), test item related clinical signs at the injection site of swelling, skin discoloration, lesions with discharge, bruising, sensitivity to touch, vocalization prior to dosing (indicative of a pain response), rings and presence of liquid material were noted from Day 2 onward. Increases in activity were noted as early as Day I during the dosing procedure.

Due to the clinical signs noted in Phases I/II/IIB/III following intravenous administration into the tail vein a decision was made to verify the injection of the test item formulation into the femoral vein. Thus Phases IV and IVB were conducted.

For Phase IV animals dosed at 30 mg/kg/day (Group 10) into the femoral vein, over 2 minutes, the primary test item related clinical sign was the presence of red liquid in the cage tray and the urogenital area. This was interpreted to be hematuria. This change was noted as of Day 2 in all Phase IV animals. Increases in activity and changes in posture (hunched back) were noted as of Day 1 and could not be excluded as test item related.

At lower doses of 7 (Group 11) and 15 (Group 12) mg/kg/day the presence of red liquid in the cage tray (hematuria) was only noted at 15 mg/kg/day as of Day 1. Other clinical signs of changes in posture (stretching) and increases in activity were noted as of Day 1 at both doses.

Body weight: For phases in which body weight evaluation was possible, there were no test item related effects noted. However a 2 to 6% decrease in body weight was noted for Group 10 animals when the end of treatment value was compared to the Day 1 value.

Macroscopic observations: For Phase III animals, numerous findings were seen at the dosing site (tail) in necropsy. In total, $8/10$ animals were affected. These findings consisted of dark focus/area/mottling ($8/10$), thickening ($6/10$) and scab ($1/10$) and were a cause of pre-terminal euthanasia.

For Phase IIB animals, findings at the dosing site (tail) were observed in $2/10$ animals dosed at 30 mg/kg/day. They consisted of dark area ($2/10$) associated with thickening and/or scab in affected animal. Enlargement of bronchial lymph node was observed in $2/10$ animals. Although a cause of this finding was unclear, in the absence of a control animal group and microscopic examination, a test item relationship cannot be confirmed or excluded. Dark area of the duodenum seen in one animal was considered to be incidental.

For Phase IV animals, no findings at the dosing site were observed. Dark focus of the lungs was observed in ⅔ animals. Although a cause of this finding was unclear, in the absence of a control animal group and microscopic examination, a test item relationship cannot be confirmed or excluded. Dark focus of the thymus in one animal was considered to be incidental or procedure-related finding.

CONCLUSIONS

The intravenous administration of cetirizine dihydrochloride by the tail vein to the Sprague Dawley rat was associated with mortality at dose levels ≥50 mg/kg (58 times of human clinical dose) for a single injection.

Repeated administration of intravenous cetirizine dihydrochloride by the tail vein at doses of 30 and 35 mg/kg/day from 2 to 7 consecutive days led to swelling, necrosis and discoloration at the injection site. These clinical signs prevented full completion of 2 phases of the study resulting in the pre-terminal euthanasia of the animals.

Hematuria was noted for cetirizine dihydrochloride repeat administration by the femoral vein for 5 consecutive days at doses of 15 and 30 mg/kg/day, but not at the dose of 7 mg/kg/day. Changes in posture and increased activity were noted at 7, 15 and 30 mg/kg/day. Therefore, it is recommended to take a conservative approach that the dose levels of 6 mg/kg/day and 13 mg/kg/day be used in the 14-day repeated dose study as the mid and high levels.

The maximum tolerated dose (MTD) for a single intravenous administration into the tail vein was determined to be 35 mg/kg (41 times of human clinical dose).

Due to the complications seen with repeated cetirizine dihydrochloride intravenous administration by the tail vein, it is recommended that the femoral vein be the route of administration for all repeat dose studies conducted, because rat's femoral vein injection is most similar to human's intravenous injection.

Example 2

14—Day Intravenous Toxicity Study in Sprague Dawley Rats

The objective of the study was to determine the toxicity and toxicokinetic (TK) profile of the test item, cetirizine dihydrochloride, following intravenous administration via the femoral vein to the rat for at least 14 days.

Methods:

The test and control items were administered to groups of rats once daily by intravenous administration into the femoral vein over 2 minutes for 14 consecutive days as described in Table 8.

TABLE 8 protocol for 14 day administration

| Group Numbers | Group Designation | Dose Level (mg/kg/day) | Dose Concentration (mg/mL) | Dose Volume (mL/kg) | Number of Animals Main Male | Main Female | TK Males | TK Females |
|---|---|---|---|---|---|---|---|---|
| 1 | Control | 0 | 0 | 1.300 | 10 | 10 | 3 | 3 |
| 2 | Low Dose | 0.86 | 10 | 0.086 | 10 | 10 | 6 | 6 |
| 3 | Mid Dose | 6 | 10 | 0.600 | 10 | 10 | 6 | 6 |
| 4 | High Dose | 13 | 10 | 1.300 | 10 | 10 | 6 | 6 |

1: The control animals were administered saline only.
2: Low Dose = human clinical dose = 10 mg per day for a 70 kg human = 0.86 mg/kg in rat
3: Mid Dose = 7 times clinical dose
4: High Dose = 15 times clinical dose The test item, test animals, clinical observation are as described in Example 1. Toxicokinetic time points were taken and the following parameters were estimated:

$t_{max}$: The time after dosing at which the maximum observed concentration was observed.

$C_{max}$: The maximum observed concentration measured after dosing.

$C_{max}/D$: The $C_{max}$ divided by the dose administered.

$t_{last}$: Time of last observed quantifiable plasma concentration.

$AUC_{0-t}$: Area under the concentration versus time curve from the start of dose administration to the time after dosing at which the last quantifiable concentration was observed, using the linear trapezoidal method.

$AUC_{0-t}/D$: The $AUC_{0-t}$ divided by the dose administered.

When data permitted, the slope of the terminal elimination phase of each
arithmetic mean concentration versus time curve was determined by log regression, and the following additional parameters were estimated:

$AUC_{0-\infty}$: Area under the plasma concentration time curve extrapolated to infinity, calculated as $AUC_{0-t}+C_{last}/\lambda Z$, where $C_{last}$ is the measured concentration at time $t_{last}$.

$AUC_{0-\infty}/D$: $AUC_{0-\infty}$ divided by the dose administered.

$AUC_{\%extrap}$: Relative percentage $AUC_{0-\infty}$ extrapolated.

$\lambda_Z$: Apparent elimination rate constant, estimated by linear regression of the terminal linear portion of the log concentration versus time curve.

$t_{1/2}$: The apparent terminal elimination half life, calculated as $\ln(2)/\lambda Z$.

$MRT_{0-\infty}$: Mean Residence Time.

V: Volume of distribution.

CL: Total body clearance.

AUCs were calculated using the linear trapezoidal rule.

Necropsy and tissue preservation were as described in Example 1.

Toxicokinetic Results:

On Day 1, rats were administered a single dose of either the control or 0.86, 6 or 13 mg/kg doses of cetirizine dihydrochloride. For all dose groups, pre-dose concentrations were below the limit of quantitation (BLQ). Cetirizine plasma concentration decreased in a bi-exponential fashion, except for the 0.86 mg/kg dose level. However, it is to be noted that the last 2 time points (12-and 24-hour time points) were BLQ for this group while the 6 and 13 mg/kg groups had measurable concentration values up to 12 hours. $C_{max}$ and $AUC_{0-t}$ values ranged from 0.876 to 14.753 µg/mL and from 0.359 to 24.903 µg*h/mL over the dose range of 0.86 to 13 mg/kg, suggesting that systemic exposure in terms of $C_{max}$ and $AUC_{0-t}$ increased approximately in a dose-proportional manner between the 0.86, 6 and 13 mg/kg for $C_{max}$ (8.800-and 1.914-fold increase) and between the 6 and 13 mg/kg dose levels for $AUC_{0-t}$ (2.966-fold). The increase between the 0.86 and 6 mg/kg doses for $AUC_{0-t}$ was approximately 23.413-fold which probably resulted from the BLQ values observed at the end of the profile at the 0.86 mg/kg dose level.

The terminal phase was well characterized with $AUC_{\%extrap}$ values <10% over the dose range. Half-life ($t_{1/2}$) ranged from 0.25 to 2.73 hours over the dose range tested. The difference observed in $AUC_{0-t}$ and $t_{1/2}$ values between the 0.86 mg/kg dose and the two other dose levels might be due to a BLQ effect, where the concentration values of the terminal portion of the 0.86 mg/kg profiles were not measurable. Apparent clearance and volume of distribution ranged from 493.615 to 2277.885 mL/h/kg and 826.373 to 2048.544 mL/kg, respectively.

Following oral administration of cetirizine, the mean peak concentration seemed similar between males and females. However, the terminal phase seemed to decrease faster for male in the 6 mg/kg group while this faster decrease was observed for the female in the 13 mg/kg group. This difference in the shape of the curve resulted in a difference in $AUC_{0-t}$ ratios, and where the female/male $C_{max}$ ratios ranged from 1.055 to 1.145 over the dose range while the $AUC_{0-t}$ female/male ratios were 1.644, 3.515 and 0.568 for the 0.86, 6 and 13 mg/kg dose levels, respectively.

Similar to Day 1, on Day 14 cetirizine plasma concentrations decreased in a bi-exponential fashion, except for the 0.86 mg/kg dose level. However, it is to be noted that measurable concentration values were observed up to 1 hour only for the 0.86 mg/kg while the 6 and 13 mg/kg groups had measurable concentration values up to 12 hours.

$C_{max}$ and $AUC_{0-t}$ values ranged from 0.865 to 13.374 µg/mL and from 0.289 to 29.783 µg*h/mL over the dose range of 0.86 to 13 mg/kg. Exposure seemed to increase in a more than dose proportional manner for $C_{max}$ between the 0.86 and 6 mg/kg dose levels (9.194 fold) while the increase seemed close to dose proportionality between the 6 and 13 mg/kg dose level (1.682 fold). In terms of $AUC_{0-t}$, exposure increased in a more than dose proportional manner over the dose range with increases of 30.760 and 3.345-fold for $6/0.86$ mg/kg and $13/6$ mg/kg ratios, respectively.

The terminal phase was well characterized with overall $AUC_{\%extrap}$ values <10% over the dose range. $AUC_{\%extrap}$ values were between 15.00 and 21.00% for both gender in the 0.86 mg/kg group and for males in the 6 mg/kg group. Half-life ($t_{1/2}$) ranged from 0.27 to 2.45 hours over the dose range tested. As observed for Day 1, the difference observed in AUC0-t and $t_{1/2}$ values between the 0.86 mg/kg dose and the two other dose levels might be due to a BLQ effect, where the concentration values of the terminal portion of the 0.86 mg/kg profiles were not measurable. Apparent clearance and volume of distribution ranged from 415.178 to 2501.648 mL/h/kg and 976.380 to 1831.114 mL/kg, respectively.

Following oral administration of cetirizine, the mean peak concentration seemed similar between males and females. However, the terminal phase seemed to decrease faster for males in the 6 mg/kg group, while this higher decrease was observed for the females in the 13 mg/kg group. This difference in the shape of the curve resulted in a difference in AUC0-t ratios, where the female/male $C_{max}$ ratios ranged from 0.771 to 1.123 over the dose range while the $AUC_{0-t}$ female/male ratios were 1.535, 3.264 and 0.592 for the 0.86, 6 and 13 mg/kg dose levels, respectively.

CONCLUSION

The intravenous administration of cetirizine dihydrochloride via the femoral vein to the rat for 14 consecutive days at doses of 0.86, 6 and 13 mg/kg/day was well tolerated.

The no observable adverse effect level (NOAEL) was established as 13 mg/kg/day (15 times of human clinical dose) based on parameters monitored on this study.

Example 3

Phase III, Multi-center, Double Blind, Randomized, Active Controlled Clinical Trial to Evaluate the Non-Inferiority Comparing Cetirizine Injection 10 mg to Diphenhydramine Injection, 50 mg, for the Treatment of Acute Urticaria Protocol This was a multi-center, parallel group, randomized, double-blind, active controlled, Phase III clinical trial of cetirizine injection 10 mg/mL versus diphenhydramine injection 50 mg/mL (Benadryl or generic equivalent) in approximately 256 subjects who either presented to Emergency Departments, hospitals, allergy clinics or Urgent Care Centers with acute urticaria, or developed acute urticaria following allergen challenge at an Allergy Clinic.

Subjects, or their guardians, signed an informed consent and were evaluated for eligibility for inclusion to treat. Eligible subjects were assessed for baseline characteristics, medical and surgical histories, concomitant medications and given a brief physical exam. Subjects were then randomized, in a 1:1 ratio, to blindly receive either cetirizine 10 mg/mL injection or diphenhydramine 50 mg/mL injection.

Efficacy assessments included patient-rated severity of pruritus, physician assessments of extent of urticaria/erythema, and sedation score. Subjects remained in the treatment center for at least after the 1 hr assessment, after which they may have been discharged at the physician's discretion.

Safety was monitored through the reporting of adverse events for up to 28 days following treatments and by monitoring vital signs at planned intervals from admission into the treating facility until readiness for discharge. After 24 and 48 hrs after discharge, subjects were contacted by phone for follow-up questions regarding recurrence of symptoms, new symptoms, additional medication taken, side effects from medication taken after discharge, relapse requiring a return to treatment center, and return to normal activities.

262 subjects at 19 study centers were enrolled and randomized to one of two treatment groups in a 1:1 ratio with 135 subjects randomized to treatment with diphenhydramine injection and 127 subjects randomized to treatment with cetirizine injection. All 262 subjects were included in the Intent-to-Treat (ITT) and Safety Populations. The Per Protocol (PP) Population included 251 (95.80%) subjects.

Diagnosis and Criteria for Inclusion:

Male or female subjects with a diagnosis of acute urticaria who needed treatment with antihistamine to alleviate their symptoms.

Subjects who were 18 years of age or older.

Subjects who were willing and able to give informed consent.

Subjects with a patient-rated pruritus severity score ≥1.

Test Product, Dose, Mode of Administration: Cetirizine, 10 mg/mL; a single 1.0 mL injection via intravenous (IV) slow push over a period of ~2 minutes; Manufacturer: Pfizer Inc., for JDP Therapeutics Inc.

Reference Treatment, Dose, Mode of Administration: Diphenhydramine, 50 mg/mL; a single 1.0 mL injection via IV slow push over a period of ~2 minutes; Manufacturer: Fresenius SE & Co. KGaA.

Duration of Treatment: Subjects received one of the assigned treatment drugs and were then followed for approximately 48 hrs.

Statistical Methods: All statistical analyses and summaries were performed using SAS for UNIX, Version 9.4 or later (SAS Institute, Cary, NC). Except where specified, all continuous variables were to be summarized with descriptive statistics (the number of subjects assessed [N], the number of non-missing values/valid cases [n], mean, standard deviation (SD), median, minimum, and maximum) and all categorical variables were to be summarized with frequency counts and percentages, by treatment group. The denominator for each percentage was the number of subjects within the population of the treatment arm (unless otherwise specified). The assumed overall type I error rate/significance level for the primary efficacy outcome was 5%, two sided, unless otherwise specified. Two-sided confidence limits were to be evaluated at 95%, p-values from inferential tests comparing specific cohorts or subgroups were compared to 0.05.

Efficacy: The primary clinical efficacy outcome measure was the 2 hr patient-rated pruritus severity score reduction/change from baseline (D2), compared between the two treatment groups (cetirizine injection, 10 mg, and diphenhydramine injection, 50 mg).

The following key secondary clinical or efficacy measures were assessed for each subject:

1. The need to return to treatment center after study discharge (i.e., second visit within approximately 24 hrs after discharge).
2. Time spent at the treating center (time from treatment administration to 'Readiness for Discharge').

The following other clinical or efficacy measures were assessed for each subject:

1. Pruritus treatment success (percent of subjects), defined as a patient who had a pruritus severity score reduction of at least 1 unit for the 2 hr patient-rated pruritus severity score from baseline (D2) compared between the two treatment groups.
2. Patient-rated pruritus severity score reduction/change from baseline at 1 hr and at 'Time of Discharge' (D1 and D3).
3. Sedation scores, at baseline, 1 hr, and/or 2 hrs, and/or 'Readiness for Discharge' (B2).
4. Physician-rated extent of urticaria/erythema scores and their reduction/change from baseline at 1 hr, 2 hrs, and 'Time of Discharge' (C1, C2, C3).
5. Use of rescue medication (e.g., epinephrine, bronchodilators, steroids, etc.) and the reasons for the use of rescue drugs.
6. 'Effectively treated' based on Investigator's opinion of Yes or No.
7. Symptom recurrence and additional symptom occurrence within approximately 24-48 hrs after subject discharge from treatment center.
8. The need for prescribed medication within approximately 24-48 hrs after discharge.
9. The need for additional medication, including any over-the-counter medications, within approximately 24-48 hrs after discharge.
10. Ability to return to normal activity after discharge.

The primary demonstration of efficacy was non-inferiority of cetirizine to diphenhydramine with regards to the change from baseline in patient-rated pruritus severity at 2 hrs post-treatment. The non-inferiority margin was set at −0.50. The null hypothesis was that cetirizine was inferior to diphenhydramine if the difference (diphenhydramine-cetirizine) was greater than −0.5 with 95% confidence. If the null hypothesis was rejected in favor of the alternative (i.e., if cetirizine was not inferior to diphenhydramine), and the treatment difference was greater than zero, then the alternative hypothesis was further refined in a stepwise manner to test for superiority of cetirizine over diphenhydramine.

The point estimate of the treatment differences of D2 (2 hr patient-rated pruritus severity score reduction/change from baseline) and the 95% confidence interval (CI) were calculated using a 2-sided t-test from a generalized linear mixed-effects model in order to adjust for any heterogeneity of treatment variance, imbalance in numbers of subjects in each treatment, and to adequately model the resulting ordinal outcome of D2. The model was also adjusted for site and site by treatment interaction. If there were treatment disparities in baseline characteristics, such as age or gender, these could have been added as covariates. The primary analysis was performed on the ITT Population with the Last Observation Carried Forward (LOCF) imputation method used to impute 2 hr scores if subjects were discharged prior to this assessment.

The following outcomes provided key support of the primary efficacy claim: return to treatment center and time spent at treatment center. The number and proportion of subjects who returned to a treatment center for additional treatment of their urticaria were summarized by response (Yes, No, or Unknown) for each follow up time and by treatment group and the difference in treatments was tested using Fisher's 2-Sided Exact Test. The time spent in a treatment center (for the initial treatment) was summarized by treatment group and the average time in the treatment center was tested for treatment difference using the same model as the primary endpoint.

Primary and key secondary outcomes were summarized for the ITT Population and also for the PP Population, as an assessment of sensitivity to protocol violations.

For other efficacy analyses, summaries were provided for each treatment group. Change from baseline at each assessment time was also provided for patient-rated pruritus severity scores change, sedation score change, and physician-rated extent of urticaria/erythema scores.

Results:

Primary Efficacy Measure: Change From Baseline in 2-Hr Patient-Rated Pruritus Severity Score". The primary efficacy measure was the change from baseline in patient-rated pruritus score assessed 2 hrs post treatment administration for the ITT Population.

The mean (SD) change from baseline in patient-rated pruritus severity score was −1.61 (0.944) for cetirizine treated subjects and −1.50 (0.984) for diphenhydramine treated subjects. The least squares estimated treatment difference was 0.06 (95% CI=−0.281, 0.396; p=0.7379). Since the lower bound of the 95% CI for the treatment different was >−0.5, effectiveness of cetirizine injection was demonstrated to be non-inferior to the effectiveness of diphenhydramine injection. However, because the lower bound was not >0 and the p-value for the treatment difference was not significant, cetirizine injection has not demonstrated superiority to diphenhydramine injection.

Need to Return to the Treatment Center The need to return to the treatment center (ED or clinic) after treatment administration was assessed for the ITT Population. Significantly fewer subjects treated with cetirizine injection returned to the treatment center compared to those treated with diphenhydramine injection (p=0.0232).

TABLE 9

Summary of Subjects Who Returned to the Treatment Center (ITT Population)

|  | Diphenhydramine Injection (N = 135) | Cetirizine Injection (N = 127) | p-value[1] |
|---|---|---|---|
| No | 116 (85.93) | 120 (94.49) |  |
| Yes | 19 (14.07) | 7 (5.51) | 0.0232 |

Time Spent in the Treatment Center: The time spent at the treatment center was 22 minutes shorter for subjects treated with cetirizine injection compared to those treated with diphenhydramine injection, based on the ITT Population analysis, and 27 minutes shorter based on the PP Population analysis.

TABLE 10

Summary of Time Spent (Hours) at the Treatment Center (ITT Population)

|  | Diphenhydramine Injection (N = 135) | Cetirizine Injection (N = 127) | p-value |
|---|---|---|---|
| n[1] | 133 | 120 |  |
| Mean (SD) | 2.07 (1.112) | 1.71 (0.868) | 0.0703[2] |
|  |  |  | 0.0052[3] |
| Median | 2.02 | 1.42 |  |
| Min, Max | 0.9, 6.1 | 0.5, 7.2 |  |

Abbreviations: Max = maximum; Min = minimum; SD = standard deviation.

[1] Nine patients had no record of discharge time or were admitted for further observations.

[2] The p-value for treatment difference in time spent in the treatment center was obtained from a 2-sided t-test from a generalized linear mixed-effects model (SAS 9.4 PROC GLIMMIX). The model consisted of the time as the dependent variable and site, treatment, and site x treatment as fixed effects. Investigator sites with no subjects in one of the two treatment groups required pooling to be included in the model. Specifically, site 2 was pooled with site 1, and site 20 was pooled with site 7.

[3] The p-value for treatment difference in time spent in the treatment center was obtained from a 2-sided t-test from a generalized linear mixed-effects model (SAS 9.4 PROC GLIMMIX). The model consisted of the time as the dependent variable, treatment as fixed effect, baseline pruritus score as a covariate, and site as a random effect. Investigator sites with no subjects in one of the two treatment groups required pooling to be included in the model. Specifically, site 2 was pooled with site 1, and site 20 was pooled with site 7.

Pruritus Treatment Success: Patient-rated pruritus severity scores were assessed at baseline, 1 hr, and/or 2 hrs, and/or 'Readiness for Discharge' in the ITT Population. Lower scores indicate no or more mild pruritus.

TABLE 11

Summary of Patient-Rated Pruritus Severity Score by Visit (ITT Population)

|  | Diphenhydramine Injection (N = 135) | Cetirizine Injection (N = 127) | Adjusted Treatment Difference | p-value[1] |
|---|---|---|---|---|
| Baseline Assessment |  |  |  |  |
| Mean (SD) | 2.19 (0.748) | 2.20 (0.727) | 0.0626 | 0.6454 |
| Min, Max | 1.0, 3.0 | 1.0, 3.0 |  |  |
| 1 Hour Assessment |  |  |  |  |
| Mean (SD) | 0.83 (0.981) | 0.81 (1.006) | −0.0527 | 0.7640 |
| Min, Max | 0.0, 3.0 | 0.0, 3.0 |  |  |
| 1 Hour Change from Baseline |  |  |  |  |
| Mean (SD) | −1.36 (0.982) | −1.39 (0.944) | −0.1154 | 0.4977 |
| Min, Max | −3.0, 1.0 | −3.0, 0.0 |  |  |
| 2 Hour Assessment |  |  |  |  |
| Mean (SD) | 0.70 (0.948) | 0.60 (0.911) | 0.1202 | 0.4650 |
| Min, Max | 0.0, 3.0 | 0.0, 3.0 |  |  |
| 2 Hour Change from Baseline[2] |  |  |  |  |
| Mean (SD) | −1.50 (0.984) | −1.61 (0.944) | 0.06 | 0.7379 |
| Min, Max | −3.0, 1.0 | −3.0, 1.0 |  |  |
| Discharge Assessment |  |  |  |  |
| Mean (SD) | 0.67 (0.937) | 0.58 (0.912) | 0.1101 | 0.4948 |
| Min, Max | 0.0, 3.0 | 0.0, 3.0 |  |  |
| Discharge Change from Baseline |  |  |  |  |
| Mean (SD) | −1.52 (0.976) | −1.62 (0.942) | 0.0475 | 0.7788 |
| Min, Max | −3.0, 1.0 | −3.0, 0.0 |  |  |

Abbreviations: Max = maximum: Min = minimum; SD = standard deviation.

[4] The nominal p-value for treatment difference in time spent in the treatment center was obtained from a 2-sided t-test from a generalized linear mixed-effects model (SAS 9.4 PROC GLIMMIX). The model consisted of the time as the dependent variable and site, treatment, and site x treatment as fixed effects. Investigator sites with no subjects in one of the two treatment groups required pooling to be included in the model. Specifically, site 2 was pooled with site 1, and site 20 was pooled with site 7.

[5] Using LOCF; if the 2 hr assessment was not available, the last recorded assessment was carried forward. If rescue occurred prior to the 2 hr assessment, then the last recorded assessment prior to rescue was carried forward.

Sedation scores: Subject-rated sedation scores were assessed at baseline, 1 hr, and/or 2 hrs, and/or 'Readiness for Discharge' in the ITT Population. Lower sedation scores indicate less sedation. Following treatment, subject-rated sedation scores increased in both treatment groups over this first hour, then declined over the second hour with cetirizine treated subjects returning to baseline sedation by 2 hrs. Subject-rated sedation scores for subjects treated with diphenhydramine injection remained above baseline through discharge.

The sedation score increase in the cetirizine injection group was significantly smaller than that observed in the diphenhydramine injection group during the study.

TABLE 12

Summary of Subject-Rated Sedation Score by Visit (ITT Population)

|  | Diphenhydramine Injection (N = 135) | Cetirizine Injection (N = 127) | Adjusted Treatment Difference | p-value[1] |
|---|---|---|---|---|
| Baseline Assessment |  |  |  |  |
| Mean (SD) | 0.39 (0.764) | 0.39 (0.667) | −0.0716 | 0.5641 |
| Min, Max | 0.0, 3.0 | 0.0, 2.0 |  |  |
| 1 Hour Assessment |  |  |  |  |
| Mean (SD) | 1.10 (0.984) | 0.62 (0.854) | 0.3848 | 0.0197 |
| Min, Max | 0.0, 3.0 | 0.0, 3.0 |  |  |
| 1 Hour Change from Baseline |  |  |  |  |
| Mean (SD) | 0.70 (0.915) | 0.24 (0.791) | 0.4564 | 0.0034 |
| Min, Max | −2.0, 3.0 | −2.0, 3.0 |  |  |
| 2 Hour Assessment |  |  |  |  |
| Mean (SD) | 0.88 (0.955) | 0.46 (0.721) | 0.2715 | 0.0768 |
| Min, Max | 0.0, 3.0 | 0.0, 3.0 |  |  |
| 2 Hour Change from Baseline |  |  |  |  |
| Mean (SD) | 0.49 (0.921) | 0.08 (0.813) | 0.3430 | 0.0292 |
| Min, Max | −2.0, 3.0 | −2.0, 3.0 |  |  |
| Discharge Assessment |  |  |  |  |
| Mean (SD) | 0.86 (0.940) | 0.46 (0.721) | 0.2344 | 0.1226 |
| Min, Max | 0.0, 3.0 | 0.0, 3.0 |  |  |
| Discharge Change from Baseline |  |  |  |  |
| Mean (SD) | 0.47 (0.888) | 0.08 (0.793) | 0.3060 | 0.0443 |
| Min, Max | −2.0, 3.0 | −2.0, 3.0 |  |  |

Abbreviations: Max = maximum: Min = minimum; SD = standard deviation.
The nominal p-value for treatment difference in time spent in the treatment center was obtained from a 2-sided t-test from a generalized linear mixed-effects model (SAS 9.4 PROC GLIMMIX). The model consisted of the time as the dependent variable and, site, treatment, and site x treatment as fixed effects. Investigator sites with no subjects in one of the two treatment groups required pooling to be included in the model. Specifically, site 2 was pooled with site 1, and site 20 was pooled with site 7.

Urticaria/Erythema Scores: Physician-rated urticaria/erythema scores were assessed at baseline, 1 hr, and/or 2 hrs, and/or 'Readiness for Discharge' in the ITT Population. Lower scores indicate a decrease in physician-rated urticaria/erythema scores or no or more mild urticaria/erythema. At baseline, the mean physician-rated urticaria/erythema scores for subjects treated with cetirizine injection and diphenhydramine injection were similar. Following treatment, physician-rated urticaria/erythema scores decreased during the study until discharge for both treatment groups. Mean physician-rated urticaria/erythema scores were statistically significantly lower in subjects treated with cetirizine injection compared to diphenhydramine injection at the 1 hr, 2 hr, and discharge assessments (nominal p=0.0355, 0.0253, and 0.0158, respectively.

TABLE 13

Summary of Physician-Rated Urticaria/Erythema Scores by Visit (ITT Population)

|  | Diphenhydramine Injection (N = 135) | Cetirizine Injection (N = 127) | Adjusted Treatment Difference | p-value[1] |
|---|---|---|---|---|
| Baseline Assessment |  |  |  |  |
| Mean (SD) | 1.84 (0.604) | 1.81 (0.632) | 0.1717 | 0.1038 |
| Min, Max | 1.0, 3.0 | 0.0, 3.0 |  |  |

TABLE 13-continued

Summary of Physician-Rated Urticaria/Erythema Scores by Visit (ITT Population)

|  | Diphenhydramine Injection (N = 135) | Cetirizine Injection (N = 127) | Adjusted Treatment Difference | p-value[1] |
|---|---|---|---|---|
| 1 Hour Assessment | | | | |
| Mean (SD) | 1.42 (0.640) | 1.27 (0.684) | 0.2415 | 0.0355 |
| Min, Max | 0.0, 3.0 | 0.0, 3.0 | | |
| 1 Hour Change from Baseline | | | | |
| Mean (SD) | −0.42 (0.580) | −0.54 (0.556) | 0.0698 | 0.4864 |
| Min, Max | −2.5, 0.5 | −3.0, 0.5 | | |
| 2 Hour Assessment | | | | |
| Mean (SD) | 1.33 (0.683) | 1.19 (0.669) | 0.2675 | 0.0253 |
| Min, Max | 0.0, 3.0 | 0.0, 3.0 | | |
| 2 Hour Change from Baseline | | | | |
| Mean (SD) | −0.51 (0.597) | −0.63 (0.617) | 0.0957 | 0.3640 |
| Min, Max | −2.5, 0.5 | −3.0, 0.5 | | |
| Discharge Assessment | | | | |
| Mean (SD) | 1.33 (0.683) | 1.17 (0.699) | 0.2920 | 0.0158 |
| Min, Max | 0.0, 3.0 | 0.0, 3.0 | | |
| Discharge Change from Baseline | | | | |
| Mean (SD) | −0.51 (0.597) | −0.65 (0.665) | 0.1203 | 0.2714 |
| Min, Max | −2.5, 0.5 | −3.0, 0.5 | | |

Abbreviations: Max = maximum; Min = minimum; SD = standard deviation.
The nominal p-value for treatment difference in time spent in the treatment center was obtained from a 2-sided t-test from a generalized linear mixed-effects model (SAS 9.4 PROC GLIMMIX). The model consisted of the time as the dependent variable and site, treatment, and site x treatment as fixed effects. Investigator sites with no subjects in one of the two treatment groups required pooling to be included in the model. Specifically, site 2 was pooled with site 1, and site 20 was pooled with site 7.

Subject Condition During 24 and 48 Hrs after Discharge: A summary of conditions, which included symptom recurrence, was obtained 24 and 48 hrs after discharge in the ITT Population. Cetirizine treated subjects experienced lower rates of recurrence of allergic symptoms compared to those treated with diphenhydramine injection as reported at 24 hrs and 48 hrs post discharge (Table 14). Cetirizine treated subjects also developed fewer other symptoms compared to those treated with diphenhydramine injection as reported at 24 hrs and 48 hrs after discharge. Higher proportions of subjects treated with cetirizine injection reported being able to return to normal daily activities at 24 hrs and 48 hrs after discharge compared to diphenhydramine injection. The proportion of subjects who needed to use medication prescribed to them at discharge were similar between treatment groups (Table 14). However, the proportion of subjects who did not need a prescription at discharge was lower in the cetirizine treated group. In addition, fewer cetirizine treated subjects needed any additional medication at 24 hrs and 48 hrs post discharge.

TABLE 14

Summary of Conditions During 24 and 48 Hrs After Discharge (ITT Population)

|  | 24 hrs | | 48 hrs | |
|---|---|---|---|---|
|  | Diphenhydramine Injection (N = 135) | Cetirizine Injection (N = 127) | Diphenhydramine Injection (N = 135) | Cetirizine Injection (N = 127) |
| Recurrence of allergic symptoms | | | | |
| Yes | 71 (52.59) | 54 (42.52) | 53 (39.26) | 36 (28.35) |
| No | 58 (42.96) | 66 (51.97) | 74 (54.81) | 85 (66.93) |
| Developed other symptoms | | | | |
| Yes | 22 (16.30) | 12 (9.45) | 13 (9.63) | 10 (7.87) |
| No | 107 (79.26) | 108 (85.04) | 114 (84.44) | 111 (87.40) |
| Needed medication prescribed at discharge | | | | |
| Yes | 69 (51.11) | 69 (54.33) | 76 (56.30) | 64 (50.39) |
| No | 39 (28.89) | 41 (32.28) | 31 (22.96) | 46 (36.22) |
| No medication prescribed | 21 (15.56) | 10 (7.87) | 20 (14.81) | 11 (8.66) |

TABLE 14-continued

Summary of Conditions During 24 and 48 Hrs After Discharge (ITT Population)

|  | 24 hrs | | 48 hrs | |
| --- | --- | --- | --- | --- |
|  | Diphenhydramine Injection (N = 135) | Cetirizine Injection (N = 127) | Diphenhydramine Injection (N = 135) | Cetirizine Injection (N = 127) |
| Needed additional medication | | | | |
| Yes | 35 (25.93) | 26 (20.47) | 26 (19.26) | 19 (14.96) |
| No | 94 (69.63) | 94 (74.02) | 101 (74.81) | 102 (80.31) |
| Returned to normal activity | | | | |
| Yes | 100 (74.07) | 103 (81.10) | 105 (77.78) | 112 (88.19) |
| No | 29 (21.48) | 17 (13.39) | 22 (16.30) | 9 (7.09) |

Summary of Treatment Success, 'Effectively Treated', and Rescue Drug Usage. The number of subjects whose pruritus was successfully treated was similar for both the cetirizine injection and diphenhydramine injection treatment groups. In addition, the number of 'effectively treated' subjects was significantly higher in the cetirizine injection treatment group. There were significantly fewer subjects in the cetirizine injection treatment group who required rescue drug usage compared to the diphenhydramine injection treatment group.

TABLE 15

Summary of Treatment Success, 'Effectively Treated', and Rescue Drug Usage

|  | Diphenhydramine Injection (N = 135) | Cetirizine Injection (N = 127) | p-value[1] |
| --- | --- | --- | --- |
| Pruritus treatment success, yes | 111 (82.22) | 110 (86.61) | 0.3957 |
| Effectively treated subjects, yes | 93 (68.89) | 103 (81.10) | 0.0200 |
| Subjects needed rescue drug, yes | 37 (27.41) | 19 (14.96) | 0.0159 |

Summary of Results for Example 3:

Cetirizine injection was demonstrated to be non-inferior to diphenhydramine injection for the mean change from baseline in patient-rated pruritus at the 2 hr assessment in the ITT Population. Similar results were observed for the PP Population. Two sites contributed only 1 subject each and were therefore pooled with larger sites, resulting in 17 pooled sites, which is a relatively large number of sites for a fixed effects model with site and site x treatment interactions. Therefore, an additional analysis of the primary endpoint measure in the ITT Population was performed using a model with site as a random factor and baseline pruritus as a covariate factor. This analysis was deemed to be a better fitting model than the a priori analysis model, but it yielded similar results as the a priori analysis model.

Significantly fewer subjects treated with cetirizine injection returned to the treatment center compared to those treated with diphenhydramine injection.

The mean 'time spent at the treatment center' was 22 minutes shorter for subjects treated with cetirizine injection than for those treated with diphenhydramine injection, based on analysis of the ITT Population with site as a fixed factor, and 27 minutes shorter based on analysis of the PP Population. As discussed above, 17 pooled sites is a relatively large number of sites for a fixed effects model with site and site x treatment interactions. Therefore, an additional analysis of the mean 'time spent at the treatment center' in the ITT Population was performed using a model with site as a random factor, which was deemed to be a better fitting model. The mean difference of 'time spent at treatment center' was statistically significant per the random effects analysis of variance on the ITT Population.

The mean change from baseline in sedation score was observed to be significantly less at all time points with cetirizine injection than with diphenhydramine injection.

Although not statistically significant, the mean change from baseline for physician-rated urticaria/erythema scores during the study was higher (i.e., more favorable) in the cetirizine injection group than the diphenhydramine injection group.

Fewer subjects treated with cetirizine injection reported recurrence of allergic symptoms, other symptoms, and the need for additional medication over 24 hrs and 48 hrs post discharge. More cetirizine treated subjects also reported being able to return to normal activities at their 24-hr or 48-hr telephone follow-up call, compared to those treated with diphenhydramine injection.

The number of 'effectively treated' subjects was significantly higher in the cetirizine injection group compared to the diphenhydramine injection treatment group.

The number of subjects whose pruritus was successfully treated was similar between treatment groups.

There were significantly fewer subjects in the cetirizine injection treatment group who required rescue drug usage compared to the diphenhydramine injection treatment group.

The terms "effective amount," "therapeutically effective amount and "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising the compound as disclosed herein required to provide a clinically significant decrease in acute urticaria.

This study demonstrated that cetirizine injection (10 mg/mL IV) is an effective alternative to or replacement for diphenhydramine injection (50 mg/mL IV) in the treatment of acute urticaria with benefits of less sedation, fewer AEs, earlier discharge, less symptom recurrence, and less need to return to the treatment center.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The terms "administer," "administering," "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

The term "acceptable" as used herein, with respect to a formulation, composition or ingredient, means having no persistent detrimental effect on the general health of the subject being treated.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A method of administering injectable cetirizine or levocetirizine to a human subject, comprising intravenously injecting the human subject in need thereof with an overdose of a maximum human daily clinical dose of the cetirizine or levocetirizine,
    wherein the human subject is a child 6 months to 5 years and the maximum human daily clinical dose of cetirizine dihydrochloride is 2.5 mg; the human subject is a child 6 to 11 years and the maximum human daily clinical dose of cetirizine dihydrochloride is 5 to 10 mg; or the human subject is an adult of adolescent 12 years older and the maximum human daily clinical dose of cetirizine dihydrochloride is 10 mg,
    wherein the overdose is no more than 14 times the maximum human daily clinical dose of the cetirizine or levocetirizine.

2. The method of claim 1, wherein the overdose is intentional.

3. The method of claim 2, wherein the human subject is not responding to the maximum human daily clinical dose.

4. The method of claim 1, wherein the human subject is suffering from acute urticaria.

5. The method of claim 4, wherein the human subject has concomitant angioedema.

6. The method of claim 1, wherein the injectable composition is a 10 mg/mL aqueous cetirizine dihydrochloride solution.

7. The method of claim 1, wherein the administering occurs in an emergency department or in an urgent care center.

8. The method of claim 1, wherein the overdose is an overdose administered, prescribed by, or suggested by a physician or health care worker.

9. The method of claim 1, wherein the maximum human daily clinical dose of the cetirizine or levocetirizine provides a highest no observable adverse effect level of the cetirizine or levocetirizine.

10. The method of claim 1, wherein the human subject is not responding to the maximum human daily clinical dose.

* * * * *